United States Patent
Foray et al.

(10) Patent No.: US 10,197,578 B2
(45) Date of Patent: Feb. 5, 2019

(54) PREDICTIVE METHOD OF CHARACTERIZING THE RADIOSENSITIVITY AND TISSULAR REACTION OF A PATIENT TO THERAPEUTIC IONIZING RADIATION

(71) Applicants: UNIVERSITE CLAUDE BERNARD LYON 1, Villeurbanne (FR); CENTRE NATIONAL DE LA RECHERCHE SCIENTIFIQUE, Paris (FR); CENTRE LEON BERARD, Lyons (FR); INSTITUT NATIONAL DE LA SANTÉ ET DE LA RECHERCHE MÉDICALE, Paris (FR)

(72) Inventors: Nicolas Foray, Meyrie (FR); Adeline Granzotto, Lyons (FR); Clément Devic, Lyons (FR)

(73) Assignees: UNIVERSITE CLAUDE BERNARD LYON 1, Villeurbanne (FR); CENTRE NATIONAL DE LA RECHERCHE SCIENTIFIQUE, Paris (FR); CENTRE LEON BERARD, Lyon (FR); INSTITUT NATIONAL DE LA SANTE ET DE LA RECHERCHE MEDICALE, Paris (FR)

( * ) Notice: Subject to any disclaimer, the term of this patent is extended or adjusted under 35 U.S.C. 154(b) by 83 days.

(21) Appl. No.: 15/119,641

(22) PCT Filed: Feb. 16, 2015

(86) PCT No.: PCT/FR2015/050365
§ 371 (c)(1),
(2) Date: Aug. 17, 2016

(87) PCT Pub. No.: WO2015/121596
PCT Pub. Date: Aug. 20, 2015

(65) Prior Publication Data
US 2017/0010279 A1   Jan. 12, 2017

(30) Foreign Application Priority Data

Feb. 17, 2014  (FR) ..................... 14 51215
Feb. 17, 2014  (FR) ..................... 14 51216
Oct. 10, 2014  (FR) ..................... 14 02281
Oct. 10, 2014  (FR) ..................... 14 02282

(51) Int. Cl.
*G01N 33/68* (2006.01)
*G01N 33/50* (2006.01)

(52) U.S. Cl.
CPC ...... *G01N 33/6881* (2013.01); *G01N 33/5005* (2013.01); *G01N 33/5014* (2013.01); *G01N 2333/47* (2013.01); *G01N 2333/4703* (2013.01); *G01N 2333/912* (2013.01); *G01N 2800/52* (2013.01)

(58) Field of Classification Search
CPC ................................................. G01N 33/5014
See application file for complete search history.

(56) References Cited

PUBLICATIONS

Kato et al. Radiation Research, 2006, 166 ;443-453.*
Suzuki et al. Radiation Research, 2006, 165:499-504.*
A. Granzotto et al., "Towards a first classification of human radiosensitivity: radiotherapy, radiodiagnosis and history of radiobiology", Centre de Recherche en Cancerologie de Lyon, Mar. 30, 2012, 1 page.
Aurelie Joubert et al., "Irradiation in Presence of Iodinated Contrast Agent Results in Radiosensitization of Endothelial Cells: Consequences for Computed Tomography Therapy", International Journal of Radiation: Oncology Biology Physics, vol. 62, No. 5, Aug. 1, 2005, 11 pages, Pergamon Press, USA.
A. Joubert et al., "Intrinsic radiosensitivity and DNA double-strand breaks in human cells", Cancer Radiotherapie, vol. 11, No. 3, Feb. 23, 2007, 14 pages, Elsevier Masson, Paris, France; (English Abstract).
Charles Thomas et al., "Low-dose hyper-radiosensitivity of progressive and regressive cells isloated from a rat colon tumour: Impact of DNA repair", International Journal of Radiation Biology, vol. 84, No. 7, Jul. 1, 2008, 16 pages. Informa Healthcare, UK.
Charles Thomas et al., "Impact of dose-rate on the low-dose hyper-radiosensitivity and induced radioresistence (HRS/IRR) response", International Journal of Radiation Biology, vol. 89, No. 10, Oct. 1, 2013, 13 pages.
C. Colin et al., "MRE11 and H2AX biomarkers in the response to low-dose exposure: balance between individual susceptibility to radiosensitivity and to genomic instability", International Journal of Low Radiation, Inderscience Publishers, vol. 8, No. 2, Dec. 13, 2011, 11 pages.
Nicolas Foray, "Les réparatoses: nouveaux concepts sur la preédiction de la radiosensibilité", Jan. 25, 2008, 37 pages.
Michel Bourguignon, "Actualités en radioprotection Seuil probabiliste chex l'adulte", Feb. 10, 2012, 39 pages.
Michel Bolla, "Echelle ASN-SFRO pour la prise en compte des événements de radioprotection affectant des patients dans le cadre d'une procédure médicale de Radiothérapie", Feb. 18, 2009, 20 pages.

* cited by examiner

*Primary Examiner* — Bin Shen
(74) *Attorney, Agent, or Firm* — Jordan IP Law, LLC; Todd A. Vaughn

(57) ABSTRACT

A method for predicting cellular, tissular, and clinical radiosensitivity, based on the determination and correlation of several cellular and enzymatic parameters.

13 Claims, 6 Drawing Sheets

PREDICTIVE METHOD OF CHARACTERIZING THE RADIOSENSITIVITY AND TISSULAR REACTION OF A PATIENT TO THERAPEUTIC IONIZING RADIATION

CROSS-REFERENCE TO RELATED APPLICATIONS

The present application is a National Stage Application of PCT International Application No. PCT/FR2015/050365 (filed on Feb. 16, 2015), under 35 U.S.C. § 371, which claims priority to French Patent Application Nos. FR 1451215 (filed on Feb. 17, 2014), FR 1451216 (filed on Feb. 17, 2014), FR 1402282 (filed on Oct. 10, 2014), and FR 14002281 (filed on Oct. 10, 2014), which are each hereby incorporated by reference in their respective entireties.

TECHNICAL FIELD

The invention relates to the field of medical radiobiology, and, more particularly the field of radiobiological laboratory methods. The invention relates to a novel method for predicting cellular, tissular and clinical radiosensitivity, based on the determination and correlation of several cellular and enzymatic parameters.

BACKGROUND

Approximately 1 to 15% of patients treated for a cancer by radiotherapy show a tissular reaction (such as dermatitis or proctitis) which can affect the successful provision of the treatment, to the extent that it may lead the physician to decide to stop the radiotherapy treatment before the end of the envisaged protocol. In addition, said tissular reaction is an indicator of a particularly high sensitivity of the patient to ionizing radiation. Moreover, radiotherapy treatment, even if broken off when the first visible tissular signs appear, can increase post-treatment morbidity or even mortality of patients, not only because it has not been possible to totally eradicate the cancer which was intended to be treated due to the premature stopping of the treatment, but also due to collateral damage to healthy tissues induced by the radiation itself.

It is also known that the question of the sensitivity of tissues to ionizing radiation is inseparable from that of the mechanisms of DNA damage repair. Indeed, at the cellular level, ionizing radiation can break some types of chemical bonds by generating free radicals (in particular by peroxidation) and other reactive species that are responsible for damage to DNA. Damage to DNA by endogenous or exogenous attack (such as by ionizing radiation and free radicals), can lead to various types of DNA damage as a function, in particular, of the energy deposited: damage to bases, single-strand breaks and double-strand breaks (DSB). Unrepaired DSB are associated with cell death, toxicity and, more specifically, radiosensitivity. Poorly repaired DSB are associated with genomic instability, mutagenic phenomena and a predisposition to cancer. The body has a specific repair system for each type of DNA damage. Mammals possess two main methods of DSB repair: repair by suture (ligation of the strands) and repair by recombination (insertion of a homologous or non-homologous strand).

It is known that the sensitivity of tissues to ionizing radiation is highly variable from one organ to another and from one individual to another; the concept of an "intrinsic radiosensitivity" was described by Fertil and Malaise in 1981. Moreover, various studies on the therapeutic effects and the side effects of radiotherapy have shown that some individuals enjoy a particularly high radioresistance, whereas other individuals, by contrast, exhibit a radiosensitivity that can lead to clinically recognized side effects, but without leading to a consequent lethal effect. Even excluding certain rare cases of extreme radiosensitivity, the genetic origin of which appears proven, it is thought that radiosensitivity generally stems from a genetic predisposition and is therefore specific to an individual. It would therefore be desirable to have a predictive testing method in order to be able to determine the maximum cumulative dose that a given patient can receive without risk. This question primarily arises in radiotherapy in the context of high ionizing doses. However, the question is also likely to be asked for any other exposure to strongly ionizing doses, equivalent to those used in radiotherapy.

It is known that two proteins from the family of kinases, commonly known as ATM and ATR, are involved in the detection, repair and signaling of DSB; their action requires at least the presence of a protein known by the designation BRCA1 and of a cascade of ordered phosphorylations of various ATM substrates (see the article by N. Foray et al., "A subset of ATM- and ATR-dependent phosphorylation events requires the BRCA 1 protein", published in The EMBO Journal vol. 22(11), p. 2860-2871 (2003)). A trial has been undertaken to use the ATM enzyme in an explanatory model of cellular radiosensitivity (see Joubert et al., "DNA double-strand break repair defects in syndromes associated with acute radiation response; At least two different assays to predict intrinsic radiosensitivity?", published in Int. J. Radiat. Biol., vol. 84(2), p. 107-125 (2008)), and this has enabled three types of radiosensitivity to be identified: radioresistant cells (termed Group I radiosensitivity), moderately radiosensitive cells (termed Group II radiosensitivity), and extremely radiosensitive cells (termed Group III radiosensitivity). However, no predictive model has been proposed on this basis. In particular no quantitative relationship has been established between the clinical data (tissular severity grade 0 to 5) and the radiobiological data. Similarly, the presentation of N. Foray, "Les réparatoses: nouveaux concepts sur la prédiction de la radiosensibilité", delivered during "Rencontres Nucléaire & Santé" on 25 Jan. 2008 (XP55131242) discusses the role of various markers pH2AX and MRE11 and their change over time in order to describe the number of radiation-induced double-strand breaks. This presentation does not mention the grades of tissular severity which quantify and list the level of radiosensitivity observed at the clinical level.

Many documents describe the conditions under which ATM can contribute to the detection and repair of DNA damage. Patent application WO 2004/013634 (KUDOS Pharmaceuticals Ltd) describes the identification of a component of the signaling pathway for ATM-dependent DNA damage, which interacts with other response factors to DNA damage, including the complex MRE11/Rad51/NBS1. Patent application US 2007/0072210 (Ouchi and Aglipay) proposes a method for screening potential therapeutic agents which promote a response to DNA damage, in which a protein known as BAAT1 (which is associated with a predisposition to breast cancer linked to the gene BRCA1) is mixed with an ATM protein and the candidate compound; if the phosphorylation of the ATM is increased with respect to a control mixture which does not contain the candidate compound, the latter is identified as a potential active ingredient promoting DNA repair. Patent application EP 2 466 310 A1 (Helmholtz Zentrum München) describes repair of double-strand breaks in DNA in the presence of the phosphorylated form of the histone H2AX (known as gamma-H2AX or g-H2AX). Application WO 00/47760 and patent U.S. Pat. No. 7,279,290 (St. Jude's Children's Research Hospital) describe the role of the kinase functional group of ATM in DNA repair.

These documents thus describe repair pathways but do not present any correlation to establish a link with clinical data.

Patent EP 1 616 011 B1 (International Centre for Genetic Engineering and Biotechnology) discloses a method for diagnosing a genetic defect in DNA repair, based on three steps: culturing of cells isolated from a sample to be tested, incubating said cells with a chimeric polypeptide, and characterizing the cellular response. Said cellular response is the rate of expression of a biochemical marker consisting of intracellular proteins of type p53, ATM, Chk1, Chk2, BRCA1, BRCA2, Nbs1, MRE11, Rad50, Rad51 and the histones. However, the radiation-induced expression cannot predict the functionality of said proteins (certain syndromes present a normal rate of expression even though the protein is mutated): these procedures are not functional tests.

Patent applications WO 01/90408, WO 2004/059004 and WO 2006/136686 (Commissariat à l'Energie Atomique) describe methods for observing DNA damage following ionizing irradiation. The first document discloses activities for incision of DNA lesions, but does not enable quantification of the enzymatic activities of DNA excision and resynthesis, nor of DSB repair. The two other documents describe quantitative evaluation of the capacity of a biological medium to repair DNA using super-coiled circular double-strand DNA (according to the third document: immobilized in a porous polyacrylamide hydrogel film). These methods do not directly concern DSB in situ in their physiological environment, and no correlation exists to validate their clinical application.

KR20030033519 proposes deducing sensitivity to radiation from the activity of a catalyst or of superoxide dismutase, KR20030033518 uses glutathione peroxidase or glucose 6-phosphate dehydrogenase. Such methods do not detect markers directly linked to DNA damage or repair.

Patent application US 2011/312514 (Dana Farber Cancer Institute) proposes using detection of FANCD2 foci as a marker. Patent application US 2007/0264648 (National Institute of Radiological Sciences) proposes to uses of DNA oligomers for predicting the appearance of side effects during radiotherapy. However, some radiosensitivities can be observed even though the concentration of FANCD2 foci is normal.

Patent applications US 2008/234946 and US 2012/041908 (University of South Florida et al.) describe a method for predicting radiosensitivity of cancerous cells, and not of healthy cells; moreover, it is based on genomic data and not on functional tests.

Patent application WO2014/154854 (Centre Hospitalier Universitaire de Montpellier) describes a method for predicting radiosensitivity of a subject through the use of at least one radiosensitivity biomarker. This method does not detect markers directly linked to DNA damage or repair; moreover, it is based on proteomic data. In addition, this patent application does not describe quantitative relations between the radiobiological data and the severity of tissular reactions.

Patent application WO 2013/187973 (University of California) describes systems and methods for determining the radiosensitivity of cells and/or of a subject with respect to a control population. More particularly, said method includes the radiation of a biological sample, the detection and quantification of radiation-induced foci within erythrocyte cells, lymphocytes or primary cells, resulting from a blood sample through the use of one or more detection markers selected from a set of markers including anti-pH2AX, anti-MRE11 and anti-ATM. Quantification of the radiation-induced foci at various post-irradiation observation times of less than two hours enables determination of the repair kinetics thereof, which is empirically correlated with the radiosensitivity of the subject. However, analysis of foci in lymphocyte cells is very difficult owing to their small nucleus. Moreover, said method does not therefore allow a practitioner to take decisions regarding patient treatment.

Patent U.S. Pat. No. 8,269,163 (New York University School of Medicine) describes a large number of proteins which can be used as markers in order to easily and rapidly appreciate the importance of accidental exposure to ionizing radiation to which a person has been subject, in order to sort patients and direct them towards an appropriate emergency treatment. Said patent relates to biological dosimetry (determination of accidental dose) while the detection of radiosensitivity is carried out using a known dose.

Patent application WO 2010/88650 (University of Texas) describes methods and compositions for identifying cancerous cells which are either sensitive or resistant to a particular radiotherapy treatment; it is therefore not applicable to all radiotherapy treatments.

Patent application WO 2010/136942 (Philips) describes a global method for monitoring a patient during radiotherapy, using biomarkers. The method comprises obtaining at least one descriptor derived from an image extracted from an imaging procedure, wherein the descriptor belongs to a tissue of interest for which radiotherapy is intended, or to a tissue in the vicinity of said target volume. The method further comprises the selection of at least one biological marker specific to a disease, suitable for detecting or quantifying side effects of radiotherapy in the tissue area of interest. The method further comprises the obtaining of at least one measurement value in vitro of the biomarker specific to the selected disease. The method further comprises processing the at least one descriptor of the at least one biomarker value in vitro by means of a correlation technique, resulting in an output signal indicative of the radiotoxicity in the tissue region of interest. However, the teaching of said patent only takes account of the dependent toxicity of the tissue and not that of the individual, and is mainly based on image analysis.

Patent application WO 2010/109357 describes a method and apparatus for scheduling of an adaptive radiotherapy protocol based on optimization of the probability of complication in normal tissues and the probability of tumor control according to markers specific to each patient. The values of markers associated with normal tissues comprise the in vitro test values, the mass spectrometry signatures of proteins, and the medical history data of the patient. The in vitro test values may be of cellular, proteomic and genetic origin, such as, but not limited to, various cell counts, HB, CRP, PSA, TNF-alpha, ferritin, transferrin, LDH, IL-6, hepcidin, creatinine, glucose, HbA1c, and the length of the telomeres. The markers from the patient history include earlier abdominal surgery, hormonal medications or anticoagulants, diabetes, age, and measurements related to tumor growth. Biomarkers not related to radiotoxicity are also envisaged, such as biomarkers associated with various forms of ablation or chemotherapy agents. However, individual radiosensitivity is not considered.

Despite this extensive prior art, the applicant notes that the patterns described above do not describe a method for quantification of individual radiosensitivity enabling an evaluation of the risk of post-radiotherapy tissular reactions, which could be employed for any patient and any type of ionizing radiation capable of inducing DSB, and which is predictive. Thus the problem of providing a method for predicting individual radiosensitivity still has no operational solution. The present invention aims to propose a novel method for predicting tissular and clinical radiosensitivity.

SUMMARY

The inventors have found, and the method according to the invention starts from said finding, that double-strand breaks (DSB) in DNA represent the type of radiation-induced damage that is most predictive of radiosensitivity when they are not repaired, and of genomic instability when they are poorly repaired. The inventors have discovered that DSB are dealt with by the majority repair mode referred to as suture, and/or by the faulty minority repair mode referred to as MRE11-dependent recombination. The balance between these two repair modes is controlled by the ATM protein. The marker pH2AX indicates a DSB recognized by the suture repair mode. The marker MRE11 indicates a DSB site which has been dealt with by the faulty MRE11-dependent repair mode. The marker pATM provides information on activation of the suture pathway by phosphorylation of H2AX and inhibition of the MRE11-dependent pathway.

The inventors have also observed a transfer of the cytoplasmic forms of the ATM protein into the cell nucleus following an oxidative-type stress, and, in particular, following a stress linked to ionizing radiation inducing DSB.

To observe damage to DNA by an exogenous attack, it is necessary to consider both the natural state of the DNA as well as the radiation-induced state of same. In addition, after irradiation, it is necessary to take account of the DNA repair, the kinetics of which depend on the repair mechanism and therefore on the type of radiation-induced damage. Further, it is known that the effectiveness and speed of DNA repair varies from one individual to another, and that there are also particular genetic conditions which lead to an exceptional radiosensitivity.

According to the invention, the problem is solved by a method based on: 1) amplifying non-transformed cells, in particular cells from skin biopsies; 2) a mechanistic model that is valid for quiescent human cells; 3) functional tests for recognition, repair and signaling of DSB that are valid whatever the therapeutic procedure.

A first subject of the invention is a method for characterizing the cellular radiosensitivity to ionizing radiation of a cellular sample taken from a patient, starting from cells taken from said patient in a non-irradiated or only slightly irradiated region, in which:

(i) said sampled cells are amplified, said amplified cells constituting the "cellular sample";

(ii) determining, on said cellular sample, the mean number of nuclear foci obtained having at least two of the markers pH2AX, pATM and MRE11 at the time of observation t (said mean numbers being called respectively NpH2AX(t), NpATM(t), NMRE11(t)), said time of observation t being the time t=0 min (referred to as t0, the non-irradiated state) and at least one observation time selected from t=t1, t2, t3 and t4, after irradiation with an absorbed dose D;

(iii) determining at least one parameter selected from the group formed by:

- the grade of severity of the post-radiotherapy tissular reaction according to the CTCAE classification, by using at least the mean numbers NpH2AX(t) and NpH2AX(tx), where tx is either t4 (preferred) or t3;
- the radiosensitivity group of the sample, by using at least the mean numbers NpH2AX(t), NpATM(t) and NMRE11(t);

and in which method t4 is a fixed value representing the time taken for the rate of DNA breaks to attain the residual value thereof, and which is advantageously chosen to be between 6 times t3 and 8 times t3, but in this case must be at least 12 hours, and preferably between 12 h and 48 h, and, which is more preferably approximately 24 hours;

t3 is a fixed value representing the time at the end of which approximately 25% of the DSB are repaired in the control cells taken from radioresistant patients, and, which is advantageously chosen to be between 3 times t2 and 5 times t2, but in this case must be at least 2.5 hours and at most 6 hours, and is preferably between 3 hours and 5 hours, and is more preferably approximately 4 hours;

t2 is a fixed value representing the time at the end of which approximately 50% of the DSB are repaired in the control cells taken from radioresistant patients, and which is advantageously chosen to be between 5 times t1 and 7 times t1, but in this case must be at least 35 minutes and at most 90 minutes, and is preferably between 45 minutes and 75 minutes, and is more preferably approximately 60 minutes;

t1 is a fixed value representing the time at the end of which the number of DSB recognized has reached a maximum in the control cells taken from radioresistant patients, and which is advantageously chosen to be between 5 minutes and 15 minutes after the end of irradiation, preferably between 7.5 minutes and 12.5 minutes, and yet more preferably to be around 10 minutes.

In one embodiment, t1 is taken to be between 8 minutes and 12 minutes, t2 is taken to be between 50 minutes and 70 minutes, t3 is taken to be between 3.5 hours and 4.5 hours, and t4 is taken to be between 22 hours and 26 hours.

In one cellular embodiment, on the said cellular sample, the mean number of micronuclei observed is determined at times t for 100 cells [in %] (this number being referred to as NMN(t)), the times t being at least t0 (non-irradiated) and t4 after irradiation with an absorbed dose D.

Said ionizing radiation is therapeutic in nature. In particular, the absorbed dose D is between 0.5 Gy and 4 Gy, preferably between 1 Gy and 3 Gy, more preferably between 1.7 Gy and 2.3 Gy, and yet more preferably 2 Gy.

In an advantageous embodiment, t1 is 10 minutes, t2 is 60 minutes, t3 is 4 hours, t4 is 24 hours, and D is 2 Gy.

For the present invention, a parameter for characterizing the cellular reaction of a patient to ionizing radiation is the severity grade according to the CTCAE classification, expressed as a dimensionless parameter, and determined as $$CTCAE = 5 - \text{Max}[NpATM(t1); NpATM(t2)]/10.$$

The use of this formula, according to the invention enables determination of the severity grade according to the CTCAE classification, carried out to obtain a decimal figure. The final value of the CTCAE obtained according to the invention is an integer corresponding to the arithmetic rounding of the value obtained by calculation. The CTCAE determined according to the invention and indicated in the application corresponds to said figure or to said integer.

In practice, this formula is particularly suitable for the determination of the severity grade of patients belonging to the type II radiosensitivity group (moderate radiosensitivity). Radiotherapy is prohibited for patients belonging to the type-III radiosensitivity group (radiosensitive patients).

In one embodiment, the radiosensitivity group is determined in the following manner:

(a) the sample is considered to be radioresistant if NpH2AX(t4)<2 and NpATM(t1)>NpATM(t2) and NpATM (t1)>30 and A<10 and B<5 and C<2; given that:

C=NpH2AX(t0)+NMN(t0);

B=% of large nuclei (greater than 150 µm2) at t0;

A=NMRE11 (t0)+Number of small pH2AX foci/cell at t0;

(b) the sample is considered to be highly radiosensitive if (NpH2AX(t4)>8 or NMN(t4)>24);

(c) The sample is considered to have a moderate radiosensitivity under all other conditions.

For some patients, DNA repair can be disrupted by continuous spontaneous production of single-strand breaks in the DNA (SSB) due to the phenomenon of hyper-recombination which is generally observed in patients that are predisposed to cancers. The spontaneous overproduction of SSB can have two non-contradictory effects: in the spontaneous state and by pH2AX marking, nuclear foci that are smaller than the pH2AX foci usually observed can appear; they reflect the presence of a large number of DSB ("small foci" phenomenon). Similarly, an overproduction of SSB may lead to chromatin decondensation, which increases the size of the cell nuclei (size generally greater than 150 µm2, corresponding to the "large nuclei" phenomenon). These two phenomena reflect a major genomic instability.

Determination of NpH2AX, NpATM and/or NMRE11 advantageously involves an immunofluorescence test.

In an advantageous embodiment, said controls cells taken from radioresistant patients have been selected as cells demonstrating an in vitro clonogenic survival rate greater than 55% after irradiation with an absorbed dose of 2 Gy.

In another embodiment, said controls cells taken from radioresistant patients have been selected as cells taken from patients who have not demonstrated significant tissular reactions during or following a radiotherapy treatment.

The method according to the invention uses at least one healthy tissue sample, preferably consisting of fibroblasts. The fibroblasts are preferably sampled from the conjunctive tissue of the patient. This sampling may be carried out by biopsy. Thus, in an advantageous embodiment, said sampled cells are fibroblast cells from a skin biopsy of a patient (typically sampled according to a method known as a "skin punch biopsy"). The tissue sample is cultivated in an appropriate culture medium.

The first step of the method according to the invention which follows the cell sampling (namely, in the preferred embodiment, the performance of the biopsy in the fibroblast line) involves characterizing the natural state of the DNA (state at t0), in other words without irradiation. This step may comprise, in particular, investigation of the size of the nuclei, the presence of micronuclei, potential spontaneous apoptotic bodies and cells with multiple lesions: the cells are observed under a fluorescence microscope. Using the dye DAPI (4',6-diamidino-2-phenylindole, CAS No. 28718-90-3 for the dihydrochloride), the rate of micronuclei is determined for 100 cells, which is an indicator of genomic instability. The number of apoptotic bodies is also determined. The population of abnormally large nuclei is also determined, the presence of which indicates chromatin decondensation.

Said ionizing radiation is defined by the absorbed dose (parameter termed D and expressed in Gray). In accordance with the present invention, the absorbed dose D is between 0.5 Gy and 4 Gy, preferably between 1 Gy and 3 Gy, more preferably between 1.7 Gy and 2.3 Gy, and still more preferably 2 Gy. These zones typically correspond to an individual radiotherapy treatment session, the number of sessions depending on the location, time and state of advancement of the tumor.

It is essential for the method according to the invention that all the time values t1, t2, t3 and t4 are defined at the start of a test series (i.e. at least for a given patient, and preferably for a plurality of patients in order to calibrate the method with respect to a statistically significant set of observations) and are the same for all determinations of all the parameters referring to said time intervals.

In the method according to the invention, t1 is advantageously between 8 minutes and 12 minutes, and/or t2 is advantageously between 50 minutes and 70 minutes, and/or t3 is advantageously between 3.5 hours and 4.5 hours, and/or t4 is advantageously between 22 hours and 26 hours; preferably all four conditions are fulfilled.

In a variant of the method that is particularly interesting and easy to standardize, t1 is 10 minutes, t2 is 60 minutes, t3 is 4 hours, t4 is 24 hours, and D is 2 Gy.

The control cells from radioresistant patients can be taken from patients selected through a clinical examination as being patients having not demonstrated significant tissular reactions during or after a radiotherapy treatment. They can also be selected as cells showing a rate of in vitro clonogenic survival greater than 55% after irradiation with an absorbed dose of 2 Gy.

Below, we describe a typical embodiment.

Cells having the markers pH2AX, pATM and/or MRE11 are observed at observation time t (said mean numbers being respectively called NpH2AX(t), NpATM(t) and NMRE11 (t)) and at least one observation time selected from t=t1, t2, t3 and t4 after irradiation with an absorbed dose D. In one embodiment, the number of foci with the marker pH2AX and the presence of multiple-lesions cells is determined. The location of the protein pATM and that of the protein MRE11 (nuclear or cytoplasmic) is noted.

This first step enables a potential genomic instability in the natural state to be identified.

The second step of the method according to the invention comprises irradiation with the desired absorbed dose D (for example 2 Gy) and evaluation of the cellular response to the ionizing radiation.

a) In a first embodiment, the repair of radiation-induced DSB by suture is investigated, which is the majority mode for repair thereof. The number of pH2AX foci per cell is determined at t4, and optionally also at t1, t2 and possibly also at t3; determination at t3 enables consolidation of the definition of the rate of kinetics from t1 to t4. In an advantageous embodiment, after duration t4, the rate of micronuclei is also determined in order to deduce the rate of radiation-induced micronuclei. This makes it possible to estimate radio-sensitivity according to the number of non-repaired DSB.

b) In a second embodiment, a more in-depth study is performed of the cellular response to ionizing radiation through measurement of the functionality of the ATM-dependent kinase activity. It is known that, in the radioresistant control cells, the phosphorylated forms of the ATM protein (pATM) are cytoplasmic in the natural state. The applicant has discovered that in the irradiated state they have a tendency to become nuclear. Once they have passed into the nucleus, the pATM forms activate the repair mechanisms by suture and inhibit the faulty MRE11-dependent repair pathway.

By way of example, if after irradiation (for example with an absorbed dose of 2 Gy) the pATM forms show a cytoplasmic localization, it can be concluded that the pATM forms do not pass or cannot normally pass from the cytoplasm to the nucleus. This can be caused by a mutation of ATM or of any other partner protein of ATM which will assist it in passing into the nucleus after irradiation: in any event, this indicates a significant radiosensitivity.

This optional determination of the location of the pATM protein is carried out at least at t1 and t2, and optionally also at t3 and t4.

c) in a third embodiment, which can be combined with the preceding embodiments, the study of the cellular response to ionizing radiation by the MRE11-dependent pathway is extended. In addition to the major repair pathway by suture, the capacity of which is quantifiable by pH2AX immunofluorescence, the applicant has identified another repair pathway, alternative to suture, and which is able to replace same in the event of deficiency: this is repair by MRE11-dependent recombination. The capacity of this pathway is quantifiable by kinetic study of immunofluorescence of the MRE11 foci. This measurement is performed at least at t1, t2 and t3, and optionally also at t4. According to the findings of the applicant, in the radioresistant control lines, MRE11 is cytoplasmic and the number of MRE11 foci is very low up to 4 hours after a dose of 2 Gy (typically 7±2 MRE11 foci); the marking becomes cytoplasmic approximately 24 hours after irradiation.

In a final step, the results are evaluated by calculating scores in order to predict the state of radiation-induced damage and/or the radiosensitivity of the patient, and in particular the CTCAE of the patient.

DRAWINGS

FIGS. 1(A), 1(B), and 1(C) respectively illustrate the change in the number of micronucleus foci (a), of pH2AX markers (b) and pATM markers (c) from non-irradiated cells as a function of the severity grade according to the CTCAE classification.

FIGS. 2(A) and 2(B) respectively illustrate the change in the number of micronuclei 24 h after irradiation as a function of the CTCAE (FIG. 2(a)) or RTOG (FIG. 2(b)) severity grades.

FIGS. 3(A), 3(B), and 3(C) respectively illustrates the kinetics over time of the mean number of foci obtained using the marker pH2AX (FIG. 3(A)), and the change in the number of pH2AX foci 24 hours after irradiation as a function of the CTCAE (FIG. 3(B)) or RTOG (FIG. 3(C)) severity grades.

Figure 5A:
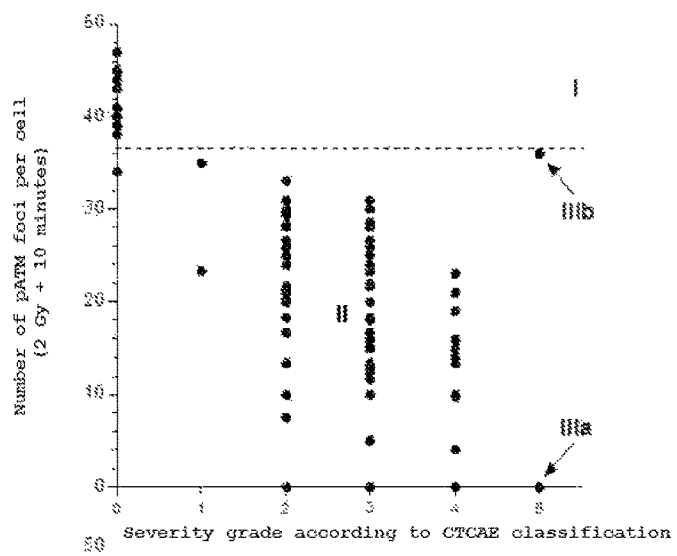
Figure 5B:
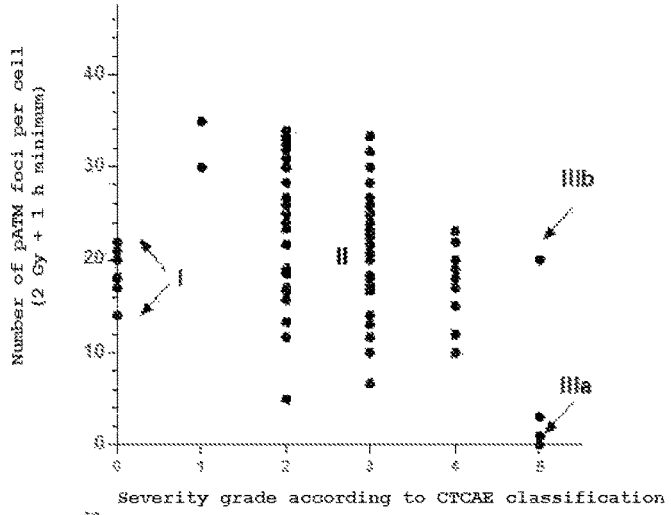
Figure 5C:
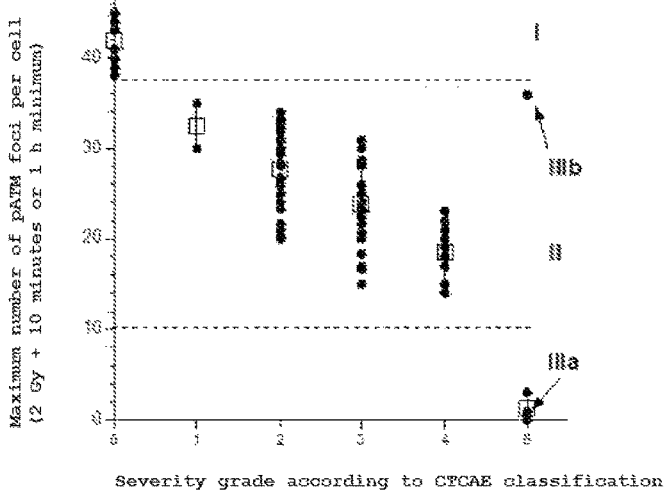

FIGS. 5(A), 5B, and 5(C) respectively illustrate the change in the number of pATM foci as a function of the CTCAE severity grades after 10 minutes (FIG. 5(A)) and 1 hour after an irradiation of 2 Gy (FIG. 5(B)), and the maximum in the number of pATM foci between the 2 values obtained at 10 minutes and 24 hours after an irradiation of 2 Gy, as a function of the CTCAE severity grades (FIG. 5(C)).

Figure 6A:
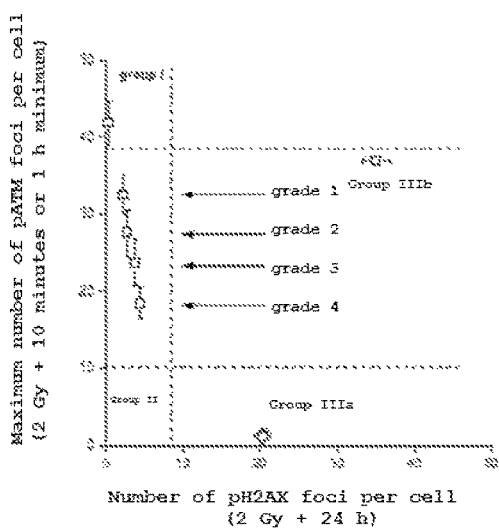

FIG. 6(A) illustrates the maximum number of foci obtained using the marker pATM as a function of the number of pH2AX foci.

Figure 6B:
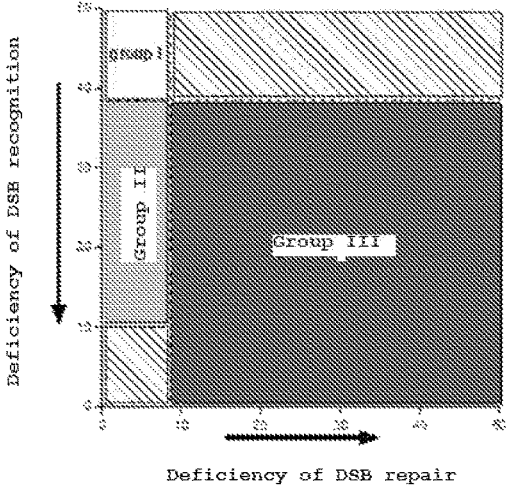

FIG. 6(B) illustrates the same data as presented in FIG. 6(A), and demonstrates the well-defined confidence zones representing the various human radiosensitivity groups (Group I, Group II and Group III).

Figure 6C:
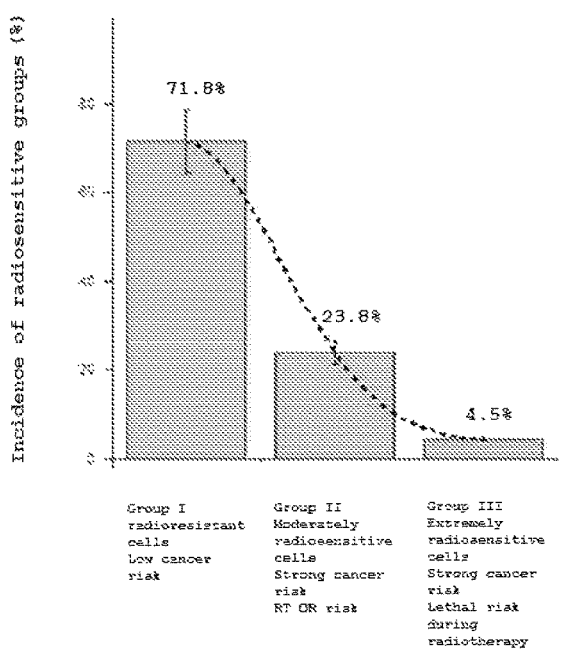

FIG. 6(C) illustrates the incidence of groups for each group type.

Figure 1A:
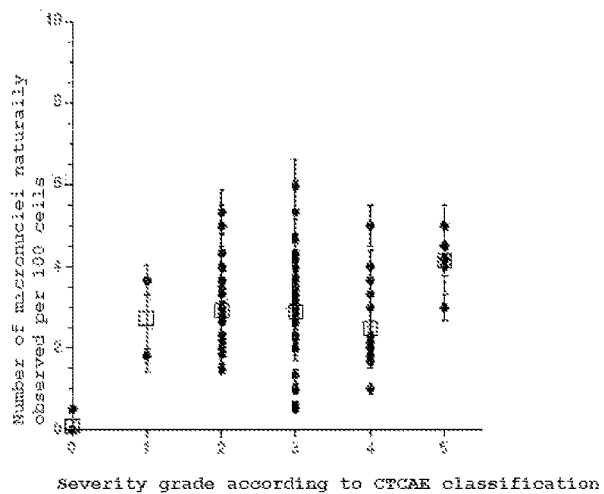
Figure 1B:
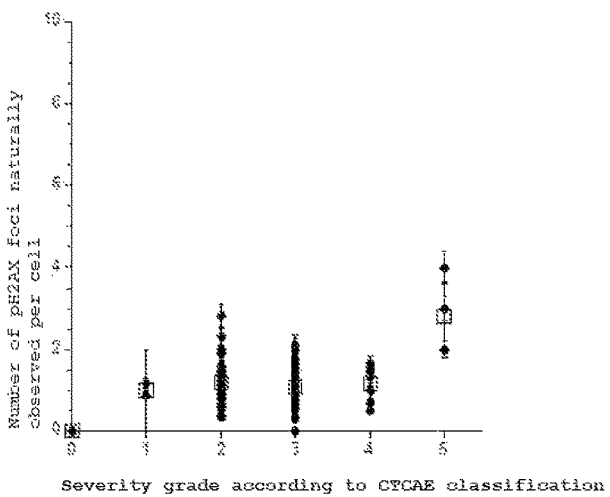
Figure 1C:
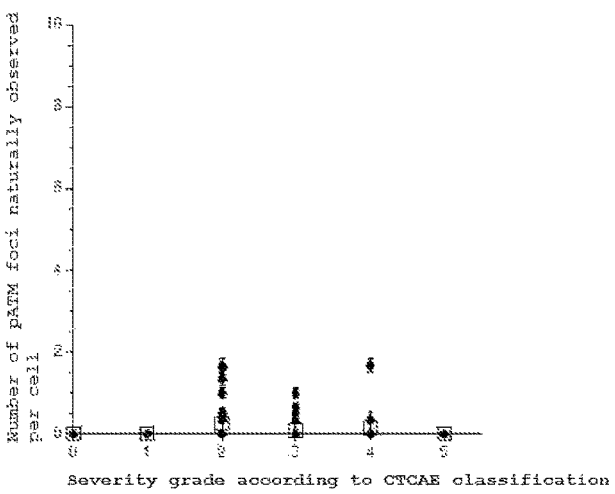

FIGS. 1 (a), (b) and (c) respectively show the change in the number of micronucleus foci (a), of pH2AX markers (b) and pATM markers (c) from non-irradiated cells as a function of the severity grade according to the CTCAE classification. The micronuclei, the pH2AX foci and pATM foci from the non-irradiated cells are not predictive of radiosensitivity.

There are two different scales for the severity of tissular reactions: the CTCAE classification and the RTOC classification.

The classification termed CTCAE (Common Terminology Criteria for Adverse Events, known in French as the "Critères d'évaluation de la morbidité selon la classification du National Cancer Institute"), published in 2006 by the National Cancer Institute of the United States of America, is a descriptive terminology of adverse events (in particular side effects) in cancer therapy.

An adverse event corresponds to any adverse and unintended sign, symptom or disease, temporally associated with the use of a medical treatment or a procedure, which may or may not be considered as being linked to the treatment or to the medical procedure. An adverse event is a unique representation of a specific event used for medical documentation and during scientific analysis.

The CTCAE provides a concise definition of each adverse event in order to clarify the meaning of the adverse event. This scale, valid for other genotoxic stresses (for example injuries caused by fire) finds particular use in radiotherapy.

The grade refers to the severity of the adverse event. The CTCAE reports 5 severity grades (1 to 5) giving unique clinical descriptions of the severity for each adverse event and described in table 1 below. Each severity grade is defined by specified tissular reactions.

TABLE 1 latest version of the CTCAE scale published by the National Cancer Institute of the United States on 14 Jun. 2010

| | |
|---|---|
| Grade 1 | Mild severity; asymptomatic or mild symptoms; clinical or diagnostic observations only; intervention not indicated |
| Grade 2 | Moderate severity; minimum, local or non-invasive action indicated; limiting age-appropriate instrumental activities of daily living (preparing meals, shopping, using the telephone, etc.) |
| Grade 3 | Serious or medically significant severity, but not immediately life-threatening; hospitalization or prolongation of hospitalization indicated; disabling event; event limiting self care activities of daily living (bathing, dressing, feeding self, using the toilet, taking medication, and not bedridden) |

TABLE 1-continued latest version of the CTCAE scale published by the National
Cancer Institute of the United States on 14 Jun. 2010

| | |
|---|---|
| Grade 4 | Life-threatening consequences; urgent intervention indicated |
| Grade 5 | Death related to the adverse event |

To these five grades, a grade 0 is added, corresponding to an absence of tissular effects.

The historical classification known as RTOG, proposed by the Radiation Therapy Oncology Group (RTOC) in 1984, covers practically all types of toxicity following radiotherapy.

However, the RTOG classification is not applicable to certain types of cancer, whereas the CTCAE classification is employed for all types of cancer.

DESCRIPTION

Figure 2A:
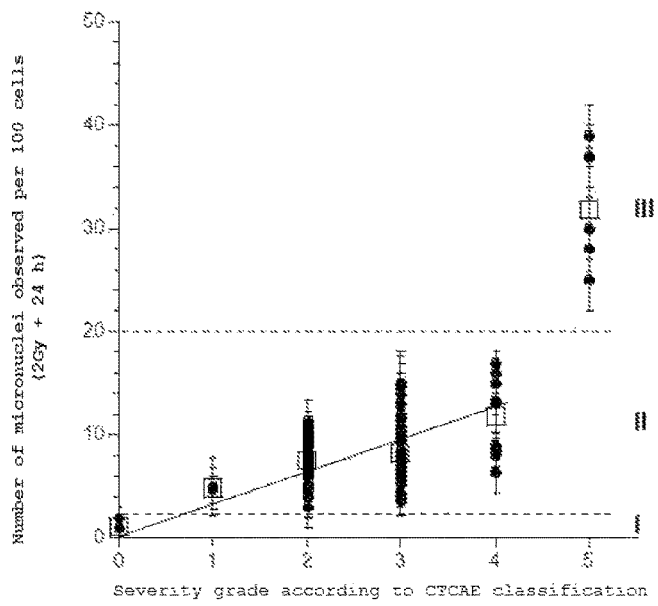
Figure 2B:
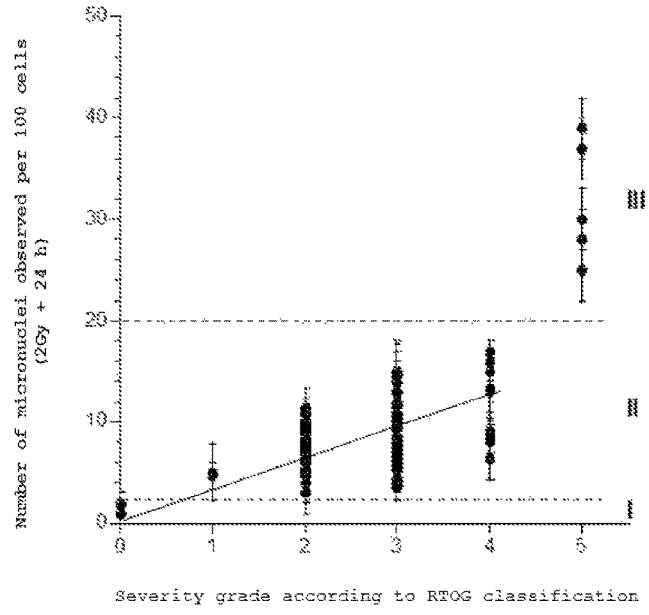

FIGS. 2 (a) and 2 (b) show the change in the number of micronuclei 24 h after irradiation as a function of the CTCAE (FIG. 2 (a)) or RTOG (FIG. 2 (b)) severity grades. The micronuclei are marked using the fluorescent marker DAPI and then quantified by fluorescence signal analysis. The radiosensitivity group (I, II, III) is indicated in Roman numerals on FIG. 2.

The number of micronuclei 24 h after irradiation only allows prediction of group III radiosensitivities.

Figure 3A:
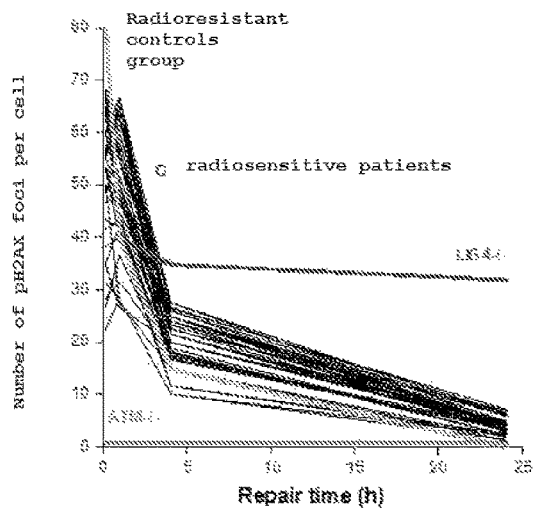
Figure 3B:
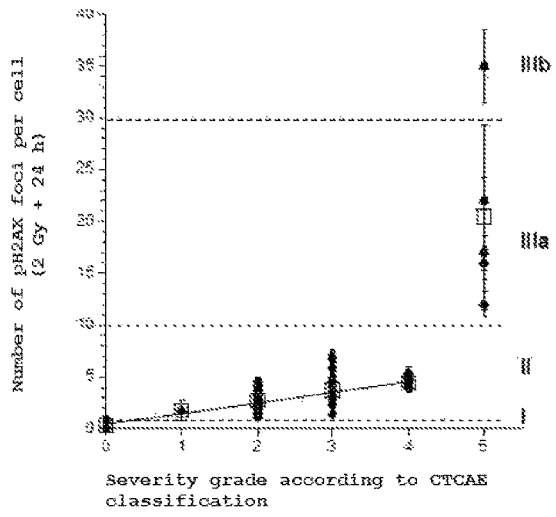
Figure 3C:
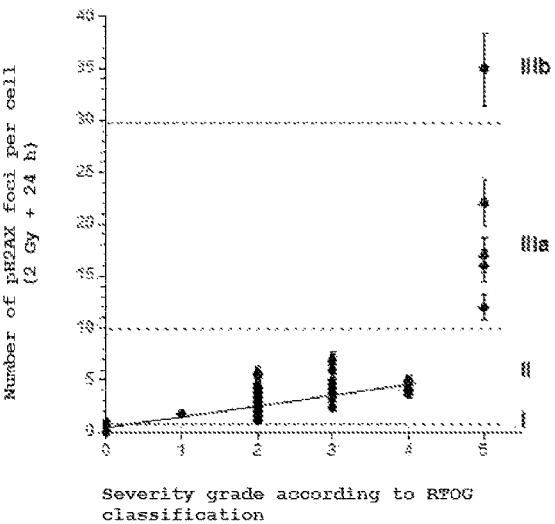

FIGS. 3 (a), (b) and (c) show the change in the number of pH2AX foci 24 hours after irradiation as a function of the CTCAE (FIG. 3 (b)) or RTOG (FIG. 3 (c)) severity grades. FIG. 3 (a) shows the kinetics over time of the mean number of foci obtained using the marker pH2AX.

The number of pH2AX foci obtained 24 hours after irradiation as a function of the CTCAE or RTOG severity grades (two different severity scales of tissular reaction) only allows prediction of radiosensitivities for group I, II or III, but not the severity grades.

Figure 4A:
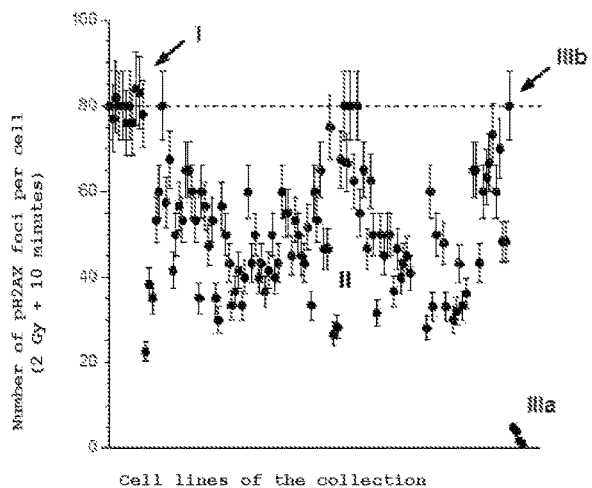
FIG. 4(A) illustrates the mean number of foci obtained using the marker pH2AX 10 minutes after irradiation with 2 Gy for all the cell lines of a collection of patient samples (skin fibroblasts), the dashed line indicating the normal incidence of DSB, which is 40 DSB per Gy per cell.
Figure 4B:
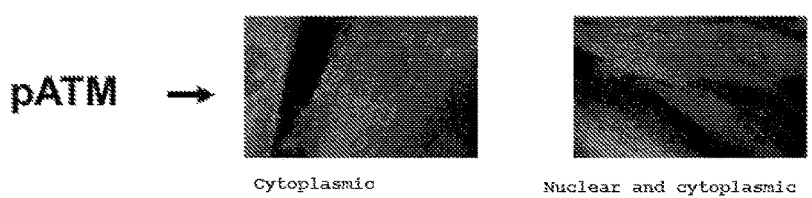
FIG. 4(B) illustrates the expression of pATM in the cytoplasm and the nucleus at various times (0 minutes, 10 minutes and 1 hour) following an irradiation of 2 Gy.
Figure 4C:
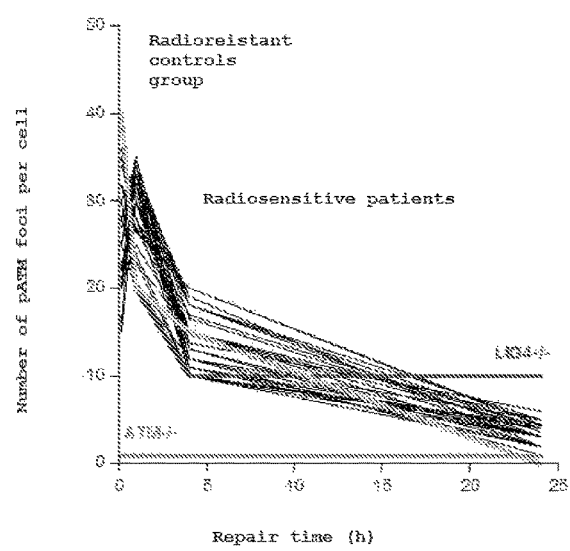
FIG. 4(C) illustrates the kinetics of the mean number of foci obtained over time with the marker pATM from cells of the collection. For convenience, the error bars relating to the measurements carried out at 10 min, 1 h, 4 h and 24 h have been omitted.

FIG. 4 (A) shows the mean number of foci obtained using the marker pH2AX 10 minutes after irradiation with 2 Gy for all the cell lines of a collection of patient samples (skin fibroblasts), the dashed line indicating the normal incidence of DSB, which is 40 DSB per Gy per cell.

FIG. 4 (A) shows that all cells coming from patients having a group II radiosensitivity are characterized by less pH2AX foci (DNA double-strand breaks (DSB)) than expected after 2 Gy. This is explained by the fact that the DSB are insufficiently recognized.

FIG. 4 (B) shows the expression of pATM in the cytoplasm and the nucleus at various times (0 minutes, 10 minutes and 1 hour) following an irradiation of 2 Gy. The corresponding immunofluorescence data are shown for non-irradiated cells and for cells irradiated with 2 Gy at 10 minutes post-irradiation.

The data presented in FIG. 4 (B), relating to the number of pATM foci, suggest a "cyto-nuclear transit" of ATM.

FIG. 4 (C) shows the kinetics of the mean number of foci obtained over time with the marker pATM from cells of the collection. For convenience, the error bars relating to the measurements carried out at 10 min, 1 h, 4 h and 24 h have been omitted. In FIGS. 4 (A) and 4 (C), each point represents the mean of three independent repetitions and the error bar represent the standard deviation for each category.

FIG. 5 shows the change in the number of pATM foci as a function of the CTCAE severity grades after 10 minutes (FIG. 5 (A)) and 1 hour after an irradiation of 2 Gy (FIG. 5 (B)). FIG. 5 (C) shows the maximum in the number of pATM foci between the 2 values obtained at 10 minutes and 24 hours after an irradiation of 2 Gy, as a function of the CTCAE severity grades, respectively shown previously in FIGS. 5(A) and 5 (B).

FIG. 5 (B) shows a grade 0, i.e. an absence of tissular effect.

FIG. 5 (C) shows, for 100 patients, the link between said radiobiological parameters and the severity grades according to the CTCAE classification. FIG. 5 (C) thus represents the clinical validation of the correlation existing between the CTCAE severity grades and maximum in the number of pATM foci between the 2 values obtained 10 minutes and 1 hour after irradiation of 2 Gy.

The radiosensitivity groups (I, II, IIIa and IIIb) are indicated with Roman numerals in FIG. 5. For FIGS. 5 (A), 5 (B) and 5 (C), each point represents the mean of three independent repetitions, for each category.

The maximum number of pATM foci between (2 Gy+10 min) or (2 Gy+1 h) makes it possible to predict all the groups as well as the severity grade of the reaction.

FIG. 6 (A) shows the maximum number of foci obtained using the marker pATM as a function of the number of pH2AX foci, previously shown in FIGS. 3 (B) and 5 (C) respectively.

FIG. 6 (B) shows the same data as presented in FIG. 6 (A), and demonstrates the well-defined confidence zones representing the various human radiosensitivity groups (Group I, Group II and Group III). Radiosensitivity is determined by recognition and repair of double-strand breaks.

FIG. 6 (C) shows the incidence of groups for each group type. Since the probability of the appearance of a given group is proportional to the inverse of the corresponding confidence zones, the normalized frequency of each group is represented by the bars in FIG. 6 (C). The dotted line corresponds to the Gaussian producing the best fit to the data (r=0.9).

General Definitions

The terms "radiation-induced damage", "radiation-induced", "radiosensitivity", "radioresistance", "radiotoxicity", and "radiotherapy" all refer to an ionizing radiation, in particular particle type radiation, such as that constituted by alpha ($\alpha$) or beta ($\beta$) particles, or high-energy electromagnetic radiation, in particular, gamma ($\gamma$) or X-ray radiation.

The term cyto-nuclear transit of ATM describes the movement undertaken by the ATM protein when passing from the cytoplasm to the nucleus, in particular, after irradiation.

Detailed Description

Below we describe an embodiment having several variants, which is suitable for a human patient.

Test Preparation

Before any cell sampling and before any manipulation of the sampled cells, the respective operators (belonging, for example, to a cytological analysis laboratory) are informed (typically by the physician) of the potential infection status of the patient by HIV or hepatitis C, in order that the operators can take the appropriate increased biological safety measures during sampling, handling and management of the cell culture.

Then, the operator takes a cell sample from the patient. Preferably, the operator takes a skin sample by biopsy; said sample can be taken advantageously according to a known method referred to as a "skin punch biopsy". The cell sample is placed in a sterile medium of DMEM+20% fetal calf serum. The sample is immediately transferred to a specialized laboratory, since the sample must not remain more than 38 hours at room temperature.

On receipt, the cell sample (typically, a biopsy) is established in the form of an amplifiable cell line without viral or chemical transformation agent according to an ancillary procedure that is well known in culture laboratories, such as that highlighted in the publication of Elkin M. et al. "The radiobiology of cultured mammalian cells", Gordon and Breach (1967). Once the number of cells is sufficient (1-3 weeks), the first experiments are performed using the method according to the invention. The cells are seeded on glass slides in Petri dishes. A number of said slides are irradiated in a medical irradiator according to a certified dosimetry with an absorbed dose D (for example 2 Gy). Another part is not irradiated and represents the natural state (absorbed dose 0 Gy).

The irradiation can be carried out, for example, using a medical accelerator which delivers 6 MV photons with an absorbed dose rate of 3 Gy min-1. After irradiation and to undergo the repair time mentioned below, the cells remain in the culture incubator at 37° C.

For the irradiated cells, characteristics corresponding to the radiation-induced state are acquired after several repair times (post-radiation repair times). Preferably at least two, and yet more preferably at least three, points are required, namely: t1, t2, t3 and t4. Said characteristics are represented by the foci corresponding to the marker pH2AX.

The cells on glass slides are then fixed, lysed and hybridized. The following procedure, which is known (see the cited publication of Bodgi et al.), can be used: the cells were fixed in 3% paraformaldehyde and 2% sucrose for 15 minutes at room temperature and permeabilized in 20 mM HEPES buffer solution (4-(2-hydroxyethyl)-1-piperazineethanesulfonic acid) at pH 7.4, 50 mM NaCl, 3 mM MgCl2, 300 mM sucrose, 0.5% Triton X-100 (a non-ionic surfactant of formula t-Oct-C6H4-(OCH2CH2)xOH with x=9-10, CAS No. 9002-93-1, supplied by Sigma Aldrich) for 3 minutes. Then the cover slides were washed in phosphate-buffered saline (known by the initials PBS) having immunological coloring. The incubation took place for 40 minutes at 37° C. in PBS with 2% bovine serum albumin (known by the initials BSA or fraction V, supplied by Sigma Aldrich) and was followed by washing with PBS. The primary antibodies, anti-pH2AX, were used at a concentration of 1:800, and the other primary antibodies at 1:100. Incubation with anti-mouse secondary antibodies FITC or anti-rabbit secondary antibodies TRITC (1:100, supplied by Sigma Aldrich) was carried out at 37° C. in 2% BSA for 20 minutes. The glass slides were treated with Vectashield™ containing DAPI (4,6-diamidino-2-phenylindole) in order to mark the nucleus. Coloration with DAPI also indirectly enables the determination of the number of cells in phase G1 (cells with homogeneous DAPI coloration), in phase S (cells with many pH2AX foci), in phase G2 (cells with heterogeneous DAPI coloration) and metaphases (visible chromosomes).

Results are obtained from said slides under immunofluorescence microscopy (Olympus model for example). The reading may be direct (typically by counting the foci over at least 50 cells in G0/G1 for each point) or by dedicated image analysis software, or even on an automated microscope; preferably the software or automated microscope methods are calibrated using manual determinations.

In order to obtain results having sufficient statistical reliability to be used as a diagnostic base, at least 3 independent series of experiments (irradiation) are carried out and the mean of each number of foci for the defined times is calculated.

Determination of Biological and Clinical Parameters
General Information and Markers Used The invention is based on, among other things, the use of data acquired for at least two of the three markers pH2AX, pATM and MRE11 on non-irradiated cells (natural state) and irradiated cells (radiation-induced state). The method is based on the kinetic study of marking by said marker as a function of the duration of repair: the samples are marked after a determined period of time from the end of irradiation, and their immunofluorescence is studied. Full kinetic curves can be measured, for example represented by 5 points advantageously situated at t0, t1 (preferably 10 minutes), t2 (preferably 1 h), t3 (preferably 4 h) and t4 (preferably 24 h), given that t0 corresponds to the state before irradiation (natural state).

However, the applicant has found that certain points (corresponding to certain repair times) are more significant than others, and that certain points are not predictive. Through judicious selection of parameters determined at given times, the number of measurements can also be reduced and thus the overall cost of the diagnosis is reduced, without diminishing the predictive power of the method. This simplified method constitutes the basis of the predictive method according to the invention.

The means of each point and each dose with each marker are calculated with the standard error of the mean (SEM) given that the sampling is n=3 (no Gaussian standard deviation of the standard error type SE).

(i) pH2AX designates the phosphorylated forms in serine 439 of the variant X of the histone H2AX which marks, according to the findings of the applicant, the number of DNA double-strand breaks (DSB) which are recognized by the reliable majority repair mode, namely suture. The marker pH2AX is essentially nuclear, uniquely in the form of nuclear foci, and only the number and size of the foci are analyzed.

(ii) pATM designates the phosphorylated forms in serine 1981 of the kinase protein ATM. According to the findings of the applicant, ATM passes from the cytoplasm to the nucleus after irradiation under normal conditions (radioresistant status). The pATM forms mainly concentrate in the cytoplasm, marking the DSB sites. The marker pATM is distinguished by a localization which may be homogeneous cytoplasmic (no cytoplasmic foci) without nuclear foci, uniquely nuclear in the form of nuclear foci only (no homogeneous nuclear localization), or cytoplasmic and nuclear foci.

(iii) MRE11 is an endonuclease which breaks DNA. According to the findings of the applicant, MRE11 marks poorly repaired DSB when the repair process is finalized. The marker MRE11 can be either cytoplasmic without foci, or cytoplasmic and nuclear without foci, or cytoplasmic and nuclear with foci.

The counter coloration with DAPI (a DNA marker known to a person skilled in the art) allows localization of the nucleus in order to locate the cytoplasmic or nuclear localization (this repair being modified for MRE11 and pATM under the influence of ionizing radiation), in order to quantify the micronuclei, apoptotic bodies and the size of the nuclei which are additional cell markers to the data on the foci.

Biological Parameters

The following are defined and determined as indicated:
NpH2AX(t), NpATM(t), NMRE11(t) the mean number of nuclear foci obtained using the markers pH2AX, pATM, and MRE11 at observation times t0 (non-irradiated) or t1, t2, t3, t4 after irradiation (absorbed dose: 2 Gy), given that determination of the parameter NpH2AX(t) is obligatory in the method according to the invention, whereas that of other parameters NpATM(t) and NMRE11(t) is optional but advantageous;

NMN(t) the number of micronuclei observed naturally (at t=t0, i.e. without irradiation) or at t=t4 after irradiation with an absorbed dose of 2 Gy for 100 cells (in %).

Predictive Evaluation

It is aimed to predict clinical or radiotherapy parameters from the measured biological data. Two levels of diagnosis are proposed:

a) a quantitative diagnosis coming directly from the mathematical value of the scores or from mathematical formulas linking the scores; the scores concerning the following two criteria:

(i) Classification of the patient in group I, II or III (criterion called the GROUP):

The definition of radiosensitivity groups (GROUP) assists the physician in determining analogies with known genetic syndromes from the scores according to the invention and from the clinical table of the patient. These groups have been defined in the publication of Joubert et al. cited above.

According to the invention, it is considered that:
if NpH2AX(t4)<2 and
if NpATM(t1)>NpATM(t2) and
if NpATM(t1)>30 and
if A<10 and
if B<5 and
if C<2
given that:
C=NpH2AX(t0)+NMN(t0);
B=% of large nuclei (greater than 150 µm2) at t0;
A=NMRE11(t0)+number of small pH2AX foci/cell at t0;
then the radiosensitivity group (GROUP criterion) is considered to be "Group 1": said cells are radioresistant.

If (NpH2AX(t4)>8 or NMN(t4)>24)
then the radiosensitivity group (GROUP criterion) is considered to be "Group III": said cells are highly radiosensitive.

For all other conditions, it is considered that the GROUP criterion is "Group II": said cells demonstrate a moderate radiosensitivity.

(ii) The severity grade of the expected tissular reaction according to the acute CTCAE classification (criteria termed CTCAE).

The classification termed CTCAE (Common Terminology Criteria for Adverse Events, known in French as the "Critères d'évaluation de la morbidité selon la classification du National Cancer Institute"), published in 2006 by the National Cancer Institute of the United States of America, is a descriptive terminology of adverse events (in particular side effects) in cancer therapy.

According to the invention, this grade is determined according to the following equation:

CTCAE=5−[max($NpATM(t1)$; $NpATM(t2)$)]/10 b) a more qualitative diagnosis, influenced by the quantitative diagnosis but taking account of possible clinical elements brought to the attention of the practitioner.

Analysis Methods and Levels

In a first embodiment, all the experimentally measured parameters are mathematically connected (for some). In the event of a conflict between the scores, certain experiments or determinations are repeated, or others are added. The level of certain parameters is only sufficient to establish one score and one diagnosis.

A second embodiment takes account of the observation that certain points are not predictive of any score: as is the case, for example for points NpH2AX(t3), NpATM(t3 and t4). This is why it is possible to envisage a restricted analysis in which only the points t0, t1, t2 and t4 are used for pH2AX, the points t0, t1 and t2 for pATM, and points t0, t1, t2, and t3 for MRE11.

This predictive method for determining the severity grade according to the CTCAE classification has been applied to healthy tissues, the majority of which are fibroblast-type connective tissue. The method can be applied to any type of cancer. The correlation obtained between pATM and CTCAE making it possible to determine the severity grade of patients according to the CTCAE classification (cf. FIG. 5 (C)) and described in the application, has been validated on patients afflicted with breast cancer, cancer of the mediastinum, all types of ENT cancer, neuroblastoma, prostate cancer, cancer of the uterus, of the ovaries and of the rectum.

The method according to the invention for determining the radiosensitivity of the sample from a patient, has been applied to tissues of the tumor cell type, cells from patients afflicted with breast cancer, prostate cancer, cancer of the uterus, ovarian cancer, cancer of the rectum, and all types of ENT cancer, glioblastoma, neuroblastoma, retinoblastoma, osteosarcoma and melanoma The invention is illustrated below by examples, which do not however limit the invention in any way. The examples focus on analysis of cell lines from patients enabling determination of the severity grade and radiosensitivity group to which the Patient Belongs.

EXAMPLES

Test Preparation

A skin cell sample was taken from a patient by biopsy using the "skin punch biopsy" method, known to a person skilled in the art. The cell sample was then placed in a sterile medium of DMEM+20% fetal calf serum. The cell sample was then immediately transferred to a specialized laboratory, in order that the sample did not remain more than 38 hours at room temperature.

On receipt, the cell sample from the biopsy was established in the form of an amplifiable cell line, following a procedure well known to culture laboratories and a person skilled in the art: by using, in particular, trypsin dispersion, the cells are again diluted in a renewed medium and so on until the desired number of cells is obtained. After obtaining a sufficient number of cells (generally after 3 weeks), the first experiments were performed using the method according to the invention. The cells were seeded on glass slides in Petri dishes. A number of said slides were irradiated in a medical irradiator according to a certified dosimetry with an absorbed dose D of 2 Gy. A further number were not irradiated, said number representing the natural state (absorbed dose 0 Gy).

Determination of the number of pH2AX, MRE11 and pATM foci in the natural state and after 10 min (t1), 1 h (t2), 4 h (t3) and 24 h (t4)) of repair post-irradiation with an absorbed dose of 2 Gy, of the number of micronuclei NMN(t) observed in the natural state and after 24 h repair time after irradiation with an absorbed dose of 2 Gy for 100 cells (in %), of the number of small pH2AX foci per cell in the natural state and of the percentage of large nuclei (greater than 150 µm2) at t0.

For the cells subjected to irradiation, the irradiation was carried out using a medical accelerator which delivers 6 MV photons with an absorbed dose rate of 3 Gy min-1.

After irradiation with an absorbed dose of 2 Gy, the cells were kept in the culture incubator at 37° C. For the irradiated cells (radiation-induced state), the samples were marked after a determined time period (post-irradiation repair time), namely: 10 min (t1), 1 h (t2), 4 h (t3) and 24 h (t4) starting from the end of the irradiation, and the mean number of nuclear foci obtained was acquired with the markers pH2AX, MRE11 and pATM at said post-irradiation repair times (10 min (t1), 1 h (t2), 4 h (t3) and 24 h (t4)). The number of micronuclei NMN(t) observed after 24 hours repair time following irradiation with the absorbed dose of 2 Gy for 100 cells (in %) was also determined by immunofluorescence analysis of said samples.

For the non-irradiated cells (natural state, i.e. at t0), the mean number of pH2AX foci in the natural state was acquired, as well as the number of small pH2AX foci per cell in the natural state, the percentage of large nuclei (greater than 150 µm2) at t0 and the number of micronuclei spontaneously observed, by immunofluorescence analysis of said cells.

The non-irradiated cells and those cells having been subjected to irradiation were then fixed, lysed and hybridized on glass slides. The cells were fixed in 3% paraformaldehyde and 2% sucrose for 15 minutes at room temperature and permeabilized in 20 mM HEPES buffer solution (4-(2-hydroxyethyl)-1-piperazineethanesulfonic acid) at pH 7.4, 50 mM NaCl, 3 mM MgCl2, 300 mM sucrose, 0.5% Triton X-100 (a non-ionic surfactant of formula t-Oct-C6H4-(OCH2CH2)xOH with x=9-10, CAS No. 9002-93-1, supplied by Sigma Aldrich) for 3 minutes. Then the cover slides were washed in phosphate-buffered saline (known by the initials PBS) having immunological coloring. The incubation took place for 40 minutes at 37° C. in PBS with 2% bovine serum albumin (known by the initials BSA or fraction V, supplied by Sigma Aldrich) and was followed by washing with PBS. The primary antibodies, anti-pH2AX, were used at a concentration of 1:800, and the other primary antibodies at 1:100. Incubation with anti-mouse secondary antibodies FITC or anti-rabbit secondary antibodies TRITC (1:100, supplied by Sigma Aldrich) was carried out at 37° C. in 2% BSA for 20 minutes.

The glass slides were then treated with Vectashield™ containing DAPI (4,6-diamidino-2-phenylindole) in order to mark the nucleus. Coloration with DAPI also indirectly enabled the determination of the number of cells in the quiescence phase G0/G1 (cells with homogeneous DAPI coloration), in synthesis phase S (cells with many pH2AX foci), in quiescence phase G2 (cells with heterogeneous DAPI coloration) and in the mitosis phase M (visible chromosomes). The counter coloration with DAPI allowed, in particular, localizing of the nucleus in order to locate the cytoplasmic or nuclear localization thereof, and thus enabled quantifying of the micronuclei present.

Results were obtained from said slides under immunofluorescence microscopy (Olympus model). The reading was performed directly by counting the foci obtained with the various markers pH2AX, pATM and MRE11 over at least 50 cells in G0/G1 for each point and by dedicated image analysis software (imageJ).

In order to obtain results having sufficient statistical reliability to be used as a diagnostic base, 3 independent series of irradiations were carried out. The mean and the standard error of the mean (SEM) for each of the numbers of foci in the natural state (t0), after 10 min (t1), 1 h (t2), 4 h (t3) and 24 h (t4)) of post-irradiation repair were calculated and are presented in the table below (cf. table 2), and this for various patient skin cell samples.

TABLE 2

Determination of the severity grade and radiosensitivity of a patient as a function of the number of pH2AX, pATM and MRE11 foci in the natural state (t0) and/or after 10 min (t1), 1 h (t2), 4 h (t3) and 24 h (t4)) of repair after irradiation with 2 Gy, of the number of micronuclei NMN(t) observed in the natural state and after 24 h repair time after irradiation with an absorbed dose of 2 Gy for 100 cells (in %), of the number of small pH2AX foci per cell in the natural state and of the percentage of large nuclei (greater than 150 µm2) at t0, and this for various patient skin cell samples.

| cell line | Number of natural pH2AX foci (at t0) | Number of pH2AX foci per cell after 24 h of repair (at t4) | Mean number of radiation-induced micronuclei after 24 hours of repair (at t4) (%) | % of large nuclei (%) | Number of small pH2AX foci at t0 | $N_{MRE11}$ (at t0) | Mean number of micronuclei (at t0) | $N_{pATM}$ after 10 min of repair (at t1) | $N_{pATM}$ after 1 h of repair (at t2) | Radio-sensitivity of the sample determined according to the invention | CTCAE Severity grade determined according to the invention |
|---|---|---|---|---|---|---|---|---|---|---|---|
| HF19 | 0 ± 0 | 0.1 ± 0.0 | 1 ± 1 | 0 | 0 | 0 ± 0 | 0 ± 0 | 40 ± 2 | 20 ± 1 | group I | 1 |
| 19HM | 0.65 ± 0.07 | 2.07 ± 0.16 | 4.67 ± 1.15 | 0 | 0 | 0 ± 0 | 4.67 ± 1.15 | 26 ± 4 | 16.7 ± 8.8 | group II | 2 |
| 29CLB | 1.45 ± 0.23 | 1.9 ± 0.34 | 10.67 ± 1.15 | 0 | 43.33 | 0.3 ± 0.3 | 4.33 ± 0.58 | 20 ± 6 | 23.3 ± 3.3 | group II | 3 |
| 01DAX | 1.38 ± 0.24 | 4.66 ± 0.79 | 10.17 ± 6.37 | 0 | 0 | 0 ± 0 | 10.17 ± 6.37 | 16.67 ± 6.67 | 23.3 ± 8.8 | group II | 3 |
| 13CLB | 0.69 ± 0.1 | 1.25 ± 0.21 | 8.33 ± 3.11 | 0 | 0 | 0 ± 0 | 3 ± 1 | 13.33 ± 3.33 | 15 ± 3 | group II | 4 |
| 35CLB | 1.09 ± 0.23 | 2.01 ± 0.15 | 9.67 ± 2 | 33 | 0 | 0 ± 0 | 2 ± 0 | 30 ± 6 | 16.7 ± 3.3 | group II | 2 |
| 01PAU | 2.45 ± 1.21 | 1.65 ± 0.13 | 5.33 ± 1.15 | 1.67 | 43.33 | 0 ± 0 | 5.33 ± 1.15 | 0 ± 0 | 23.3 ± 4.4 | group II | 3 |
| AT2EM | 4.00 ± 1.00 | 16.00 ± 4.00 | 25.00 ± 3.00 | 5 | 100 | 0 ± 0 | 25.0 ± 3.0 | 0 ± 0 | 1 ± 0 | group III | 5 |
| AT5B1 | 3.00 ± 1.00 | 17.00 ± 6.00 | 30.00 ± 3.00 | 5 | 100 | 0 ± 0 | 30 ± 3 | 0 ± 0 | 0 ± 0 | group III | 5 |
| AT4B1 | 2.00 ± 1.00 | 22.00 ± 4.00 | 39.00 ± 3.00 | 5 | 100 | 0 ± 0 | 4 ± 1 | 0 ± 0 | 3 ± 1 | group III | 5 |
| AT1BR | 2.00 ± 1.00 | 12.00 ± 4.00 | 28.00 ± 3.00 | 5 | 100 | 0 ± 0 | 4.2 ± 1.0 | 0 ± 0 | 1 ± 0 | group III | 5 |
| 180BR | 3.00 ± 1.00 | 35.00 ± 3.00 | 37.00 ± 3.00 | 5 | 100 | 0 ± 0 | 4.5 ± 2.0 | 36 ± 2 | 20 ± 1 | group III | — |

Predictive evaluation of the severity grade and radiosensitivity of the sample

Cases of post-irradiation death (severity grade 5 according to the CTCAE classification) have been described in the literature since the 1970s up to the present day and systematically correspond either to cases of Ataxia telangiectasia or to cases where the patient obtains ligase 4 by mutation (see the article of A. Joubert et al., "DNA double-strand break repair defects in syndromes associated with acute radiation response: At least two different assays to predict intrinsic radiosensitivity?" published in International Journal of Radiation Biology, vol. 84(2), p 107-125 (2008)). On the basis of these retrospective data and knowing the total dose accumulated during these radiotherapy sessions, the parallel with the number of corresponding non-repaired double-strand breaks (DSB) could be made. Indeed, the number of non-repaired double-strand breaks has been measured in a large number of ataxic lines and for the unique case of LIG4 mutation (cell line 180BR). These lines systematically demonstrate a rate of non-repaired breaks exceeding the lethal threshold after one dose. The values for cell lines from patients AT and 180BR, given in table 2, contain proof of the determination of the threshold above which the number of non-repaired breaks is lethal for the patient. For these particular cases, the corresponding CTCAE grade is 5 (=death).

Severity grades 2 to 4 concern tissue reactions (e.g. dermatitis, proctitis, etc.). Severity grade 1 involves bearable side effects which are often confused, according to practitioners, with grade 0 (absence of an effect). FIG. 6 (A) representing the maximum number of foci obtained with marker pH2AX after 24 hours of post-irradiation repair as a function of the maximum number of pATM foci of different patients, demonstrates the correlation that exists between the severity grade according to the CTCAE classification and these parameters.

Thus, for various patient skin cell samples (cf. table 2), the severity grade according to the CTCAE classification has been determined using the formulas described above, namely:

$$CTCAE=5-Max[NpATM(t1); NpATM(t2)]/10.$$

This formula is particularly suitable for the determination of the severity grade of patients belonging to the type-II radiosensitivity group (moderate radiosensitivity). All patients belonging to radiosensitivity group type III (radiosensitive patients) present, and must present, severity grade 5. Radiotherapy is prohibited for said radiosensitive patients.

In practice, the radiosensitivity group of the patient is determined before the severity grade according to the CTCAE classification, in order to attribute the patient with a correct severity grade value. Currently, only one cell line case has not validated the formula for determining the severity grade according to the preceding formula. This is the case of the cell line (180BR) belonging to a type-III radiosensitivity group, for which the severity grade according to the CTCAE was calculated to have a value of 1 based on the preceding formula. However, the formula predicting the severity grade should advantageously be used after having determined the radiosensitivity group (group I, II or III) of the patient. Thus, according to the invention, patient 180BR indeed belongs to group III (hyper-radiosensitivity) and therefore, as such should not be subject to radiation under any pretext. On the other hand, the severity grade of the patients has been validated for all the other cell lines.

The radiosensitivity group of the sample has been determined using the formulas described above, in the following manner:
(a) the radioresistant sample is considered if NpH2AX (t4)<2 and NpATM(t1)>
NpATM(t2) and NpATM(t1)>30 and A<10 and B<5 and C<2; given that:
C=NpH2AX(t0)+NMN(t0);
B=% of large nuclei (greater than 150 μm2) at t0;
A=NMRE11(t0)+Number of small pH2AX foci/cell at t0;
(b) the sample is considered to be highly radiosensitive if (NpH2AX(t4)>8 or NMN(t4)>24);

(c) The sample is considered to have a moderate radiosensitivity under all other conditions.

The quantitative values of the severity grade according to the CTCAE classification and of the radiosensitivity of the sample are presented in table 2.

What is claimed is:
1. A method for characterizing a radiosensitivity to ionizing radiation of a cellular sample obtained from cells taken from a patient in a non-irradiated or only slightly irradiated zone, the method comprising:
amplifying said sampled cells, said amplified cells constituting the cellular sample;
determining on said cellular sample a mean number of nuclear foci obtained having at least two markers pH2AX, pATM, and MRE11 at a time of observation t, wherein said mean numbers are called respectively $N_{pH2Ax}(t)$, $N_{pATM}(t)$, $N_{MRE11}(t)$, said observation time t being a time t =0 min (referred to as t0, a non-irradiated state) and at least one observation time selected from the group consisting of t =t1, t2, t3 and t4 after irradiation with an absorbed dose D;
determining at least one parameter selected from the group consisting of:
a severity grade of a post-radiotherapy tissular reaction according to a Common Terminology Criteria for Adverse Events (CTCAE) classification, by using at least the mean numbers $N_{pH2Ax}(t)$ and $N_{pH2Ax}(tx)$ where tx is either t4 (preferred) or t3;
the radiosensitivity of the sample, by using at least the mean numbers $N_{pH2Ax}(t)$, $N_{pATM}(t)$, and $N_{MRE11}(t)$;
wherein:
t4 is a fixed value representing a time taken for a rate of DNA breaks to attain a residual value thereof, and which is chosen to be between 6 times t3 and 8 times t3, or approximately 24 hours;
t3 is a fixed value representing a time at an end of which approximately 25% of the double-strand breaks (DSB) are repaired in control cells taken from radioresistant patients, and which is chosen to be between 3 times t2 and 5 times t2, or approximately 4 hours, wherein the controls cells taken from radioresistant patients have been selected as cells demonstrating an in vitro clonogenic survival rate greater than 55% after irradiation with an absorbed dose of 2 Gy;
t2 is a fixed value representing a time at the end of which approximately 50% of the DSB are repaired in the control cells taken from radioresistant patients, and which is between 5 times t1 and 7 times t1, or approximately 60 minutes; and
t1 is a fixed value representing a time at the end of which the number of DSB recognized has reached a maximum in the control cells taken from radioresistant patients, and which is around 10 minutes after the end of irradiation;
wherein:
determining the severity grade according to the CTCAE classification is expressed as a dimensionless parameter: CTCAE=5 - Max[$N_{pATM}(t1)$; $N_{pATM}(t2)$]/10; and
wherein:
determining the radiosensitivity is determined by:
the radioresistant sample is considered radiosensitive if $N_{pH2Ax}(t4)$<2 and $N_{pATM}(t1)$>$N_{pATM}(t2)$ and $N_{pATM}(t1)$>30 and A<10 and B<5 and C<2; given that:

C=$N_{pH2Ax}(t0)+N_{MN}(t0)$ (a mean number of micronuclei observed at time t0 (non-irradiated) for 100 cells [in %]);

B=% of large nuclei (greater than 150 µm²) at t0; and

A=$N_{MRE11}(t0)$+Number of small pH2AX foci/cell at t0;

the sample is considered to be highly radiosensitive if ($N_{pH2Ax}(t4)>8$ or $N_{MN}(t4)>24$); and the sample is considered to have a moderate radiosensitivity under all other conditions.

2. The method of claim 1, further comprising determining, on said cellular sample, a mean number of micronuclei observed at time t for 100 cells [in %] (this number being referred to as $N_{MN}(t)$), the time t being at least t0 (non-irradiated) and t4 after irradiation with an absorbed dose D.

3. The method of claim 1, further comprising determining the mean numbers $N_{pH2Ax}(t)$ at t=t0, t1, t2 and t4 and the numbers $N_{pATM}(t)$ at t=t0, t1 and t2, and the numbers $N_{MRE11}(t)$ at t=t0, t1, t2 and t3.

4. The method of claim 1, wherein said sampled cells are fibroblast cells taken from a skin biopsy of the patient.

5. The method of claim 1, wherein an absorbed dose D is 2 Gy.

6. The method of claim 1, wherein:
t1 is between 8 minutes and 12 minutes;
t2 is between 50 minutes and 70 minutes;
t3 is between 3.5 hours and 4.5 hours; and
t4 is between 22 hours and 26 hours.

7. The method of claim 6, wherein:
t1 is 10 minutes;
t2 is 60 minutes;
t3 is 4 hours;
t4 is 24 hours; and
an absorbed dose D is 2 Gy.

8. The method of claim 1, wherein determining $N_{pH2AX}$, $N_{pATM}$ and/or $N_{MRE11}$ involves an immunofluorescence test.

9. The method of claim 1, wherein the controls cells from radioresistant patients have been selected as cells taken from patients who have not demonstrated significant tissular reactions during or following a radiotherapy treatment.

10. The method of claim 1, further comprising determining a radiosensitivity group score (GROUP).

11. The method of claim 10, wherein the radiosensitivity group (GROUP criterion) is considered to be "Group I" (radioresistant cells):
if $N_{pH2Ax}(t4)<2$; and
if $N_{pATM}(t1)>N_{pATM}(t2)$; and
if $N_{pATM}(t1)>30$; and
if A<10; and
if B<5; and
if C<2;
where C=$N_{pH2Ax}(t0)+N_{MN}(t0)$ (a mean number of micronuclei observed at time t0(non-irradiated) for 100 cells [in %]), B=% of large nuclei (greater than 150 µm²) at t0, and A=$N_{MRE11}(t0)$+Number of small pH2AX foci/cell at t0.

12. The method of claim 10, wherein the GROUP criterion is considered to be "Group III" (highly radiosensitive cells) if:
$N_{pH2Ax}(t4)>8$; or
$N_{MN}(t4)$ (a mean number of micronuclei observed at time t4(after irradiation) for 100 cells [in %])>24.

13. The method of claim 10, wherein for all other conditions, the GROUP criterion is considered to be "Group II" (cells exhibiting moderate radiosensitivity).

* * * * *